US012745930B2

(12) United States Patent
Park et al.

(10) Patent No.: US 12,745,930 B2
(45) Date of Patent: Sep. 29, 2026

(54) GLUCOSE MONITORING SENSOR OF VOLTAGE MEASUREMENT TYPE INCLUDING A SUPERCAPACITOR AND A CONTINUOUS MEASUREMENT METHOD OF GLUCOSE USING THE SAME

(71) Applicant: Industry-Academic Cooperation Foundation, YONSEI UNIVERSITY, Seoul (KR)

(72) Inventors: Jin Woo Park, Seoul (KR); Hye Jun Kil, Seoul (KR)

(73) Assignee: Industry-Academic Cooperation Foundation, YONSEI UNIVERSITY, Seoul (KR)

( * ) Notice: Subject to any disclaimer, the term of this patent is extended or adjusted under 35 U.S.C. 154(b) by 344 days.

(21) Appl. No.: 18/390,749

(22) Filed: Dec. 20, 2023

(65) Prior Publication Data

US 2024/0415416 A1 Dec. 19, 2024

(30) Foreign Application Priority Data

Jun. 19, 2023 (KR) ........................ 10-2023-0077845

(51) Int. Cl.
*A61B 5/145* (2006.01)
*A61B 5/00* (2006.01)
*A61B 5/1486* (2006.01)

(52) U.S. Cl.
CPC ........ *A61B 5/14514* (2013.01); *A61B 5/0015* (2013.01); *A61B 5/14532* (2013.01); *A61B 5/14865* (2013.01); *A61B 2560/0443* (2013.01); *A61B 2560/0462* (2013.01); *A61B 2562/028* (2013.01); *A61B 2562/046* (2013.01)

(58) Field of Classification Search
CPC .............. A61B 5/14514; A61B 5/0015; A61B 5/14532; A61B 5/14865; A61B 2560/0443; A61B 2560/0462; A61B 2562/028; A61B 2562/046; A61B 2560/0214; A61B 5/14503; A61B 5/6833; A61B 5/685; A61B 5/0002; A61B 5/6801; A61B 5/277;
(Continued)

(56) References Cited

FOREIGN PATENT DOCUMENTS

| | | | | |
|---|---|---|---|---|
| CN | 110044986 A | * 7/2019 | ......... | G01N 27/3278 |
| KR | 20200113997 A | * 10/2020 | ............. | A61B 5/746 |

(Continued)

OTHER PUBLICATIONS

Kil et al., ACS Appl. Mater. Interfaces Jan. 13, 2022, 14,3838-3848, a self-charging supercapacitor for a patch-type Glucose Sensor (Year: 2022).*

*Primary Examiner* — Brian L Casler
(74) *Attorney, Agent, or Firm* — Bridgeway IP Law Group, PLLC; Jihun Kim

(57) ABSTRACT

A voltage measurement type glucose sensor comprises a microneedle array including a flat part and a plurality of microneedles located on one surface of the flat part; an enzyme layer located on a surface of the plurality of microneedles and including glucose oxidase; a supercapacitor located on the other side of the flat part; and a wireless communication module electrically connected to the supercapacitor, and a glucose measurement method using the same. The glucose sensor is self-driving without the need to apply separate external power, improving the lifespan of the device and enabling close monitoring of accurate glucose levels in real time.

14 Claims, 6 Drawing Sheets

(58) Field of Classification Search
CPC ......... A61B 5/262; A61B 5/266; A61B 5/268; C12Q 1/006; C12Q 2565/607; G01N 33/66
USPC .......................................................... 600/345
See application file for complete search history.

(56) References Cited

FOREIGN PATENT DOCUMENTS

| | | | | | |
|---|---|---|---|---|---|
| KR | 20220050350 A | * | 4/2022 | ......... A61B 5/14532 |
| KR | 10-2427230 B1 | | 7/2022 | |

* cited by examiner

GLUCOSE MONITORING SENSOR OF VOLTAGE MEASUREMENT TYPE INCLUDING A SUPERCAPACITOR AND A CONTINUOUS MEASUREMENT METHOD OF GLUCOSE USING THE SAME

CROSS REFERENCE TO RELATED APPLICATION

The present application claims priority to Korean Patent Application No. 10-2023-0077845, filed on Jun. 19, 2023, the entire contents of which is incorporated herein for all purposes by this reference.

BACKGROUND OF THE INVENTION

Field of the Invention

The disclosure relates to a voltage measurement type glucose sensor including a supercapacitor and a continuous glucose measurement method using the same.

DESCRIPTION OF THE RELATED ART

In the past, diabetes was considered a geriatric disease that mainly occurred in people in their 60s or older, but recently, due to westernized eating habits, lack of exercise, and stress, the number of diabetes patients is rapidly increasing among young people under 40 years of age. If hyperglycemia continues, serious complications such as cardiovascular disease, stroke, vision damage, and skin necrosis occur, so it is important to minimize the risk of complications through thorough glucose management.

Conventionally, glucose has been measured through blood sampling, but blood sampling causes pain to a subject to be tested and there is a problem in that continuous changes in glucose cannot be identified. To solve this problem, a continuous glucose monitoring (CGM) device, which measures glucose in blood by detecting glucose in tissue fluid with a microneedle inserted into the skin, has been developed. However, in the commercialized continuous glucose monitoring device, as glucose is measured due to tissue fluid moving from the surface of a needle inserted into the skin to the inside of the sensor due to capillary action, a time difference occurs in the reflection of glucose. In addition, the conventional continuous glucose measuring device must measure the intensity of electric current electrochemically generated during an enzyme reaction to measure glucose in blood, but in order to measure the current flowing between electrodes, it is necessary to apply a certain voltage, which causes a problem that reduces the lifespan of the device.

Accordingly, as disclosed in KR Registered Patent No. 10-2427230, a glucose sensor using a self-charging capacitor has been developed. However, the above glucose sensor qualitatively determines glucose information according to the intensity of light from a light emitting unit, so there is a problem in that accuracy when measuring glucose is low and the measured glucose information cannot be recorded, making it impossible to monitor trends in glucose changes.

On the other hand, when a wireless communication device is added to transmit and record the measured glucose signal to the outside, tens of microwatts of power are consumed for one measurement, which places a large burden on the power source of the glucose meter. As a result, as the glucose measurement time interval increases to minimize power consumption, it is difficult to closely observe glucose changes in real time.

DOCUMENTS OF RELATED ART (Patent Document 1) KR Registered Patent No. 10-2427230

SUMMARY OF THE INVENTION

An object of the disclosure is to solve the problems of the prior art, and to provide a glucose sensor that operates independently without a need for a separate external power source, improving a device's lifespan, and a continuous glucose measurement method using the same.

Another object of the disclosure is to provide a glucose sensor in which the discomfort or foreign body sensation felt by a user who wears the glucose sensor is significantly reduced.

In addition, an object of the disclosure is to provide a glucose sensor that can measure glucose values with high accuracy and closely monitor changes in glucose, and a continuous glucose measurement method using the same.

A glucose sensor according to the disclosure comprises a microneedle array including a flat part and a plurality of microneedles located on one surface of the flat part; an enzyme layer located on a surface of the plurality of microneedles and including glucose oxidase; a supercapacitor located on the other side of the flat part; and a wireless communication module electrically connected to the supercapacitor.

In the glucose sensor of the disclosure, the microneedle array may be electrically connected to one electrode of the supercapacitor.

In the glucose sensor of the disclosure, a charge generated by oxidation of glucose in the enzyme layer may be stored in the supercapacitor.

In the glucose sensor of the disclosure, the glucose sensor may operate without separate external power.

In the glucose sensor of the disclosure, the microneedle array may include a conductive polymer.

The glucose sensor of the disclosure may further comprise a porous membrane located on the enzyme layer.

In the glucose sensor of the disclosure, the porous membrane may include a PVDF-based polymer.

In the glucose sensor of the disclosure, an average pore size of the porous membrane may be 200 to 500 nm.

In the glucose sensor of the disclosure, an average porosity of the porous membrane may be 50 to 60%.

In the glucose sensor of the disclosure, the supercapacitor may include a first electrode located on one surface of a first current collector; a second electrode located on one surface of a second current collector and spaced apart from the first electrode; and an electrolyte located between the first electrode and the second electrode.

In the glucose sensor of the disclosure, the electrolyte may include a gel polymer electrolyte.

In the glucose sensor of the disclosure, the wireless communication module may include Bluetooth.

The disclosure provides a continuous glucose measurement method using the above-described glucose sensor.

A continuous glucose measurement method according to the disclosure comprises the steps of (S1) inserting the glucose sensor of any one of claims 1 to 12 into a skin to collect tissue fluid; (S2) storing charge generated by oxidation of glucose contained in the tissue fluid in the supercapacitor; (S3) quantifying a glucose level by measuring a voltage change of the supercapacitor; and (S4) transmitting the glucose level to an external device.

In the continuous glucose measurement method, the external device may record the glucose level in real time.

The glucose sensor and continuous glucose sugar measurement method using the same according to the disclosure are self-driving without the need for a separate external power source, thereby improving the device's lifespan.

In addition, the disclosure may provide a glucose sensor in which discomfort or foreign body sensation felt by the user is significantly reduced due to excellent flexibility.

Furthermore, the glucose sensor and continuous glucose measurement method using the same according to the disclosure can measure glucose values with high accuracy and closely monitor glucose changes in real time.

DETAILED DESCRIPTION OF THE INVENTION

Figure 1:
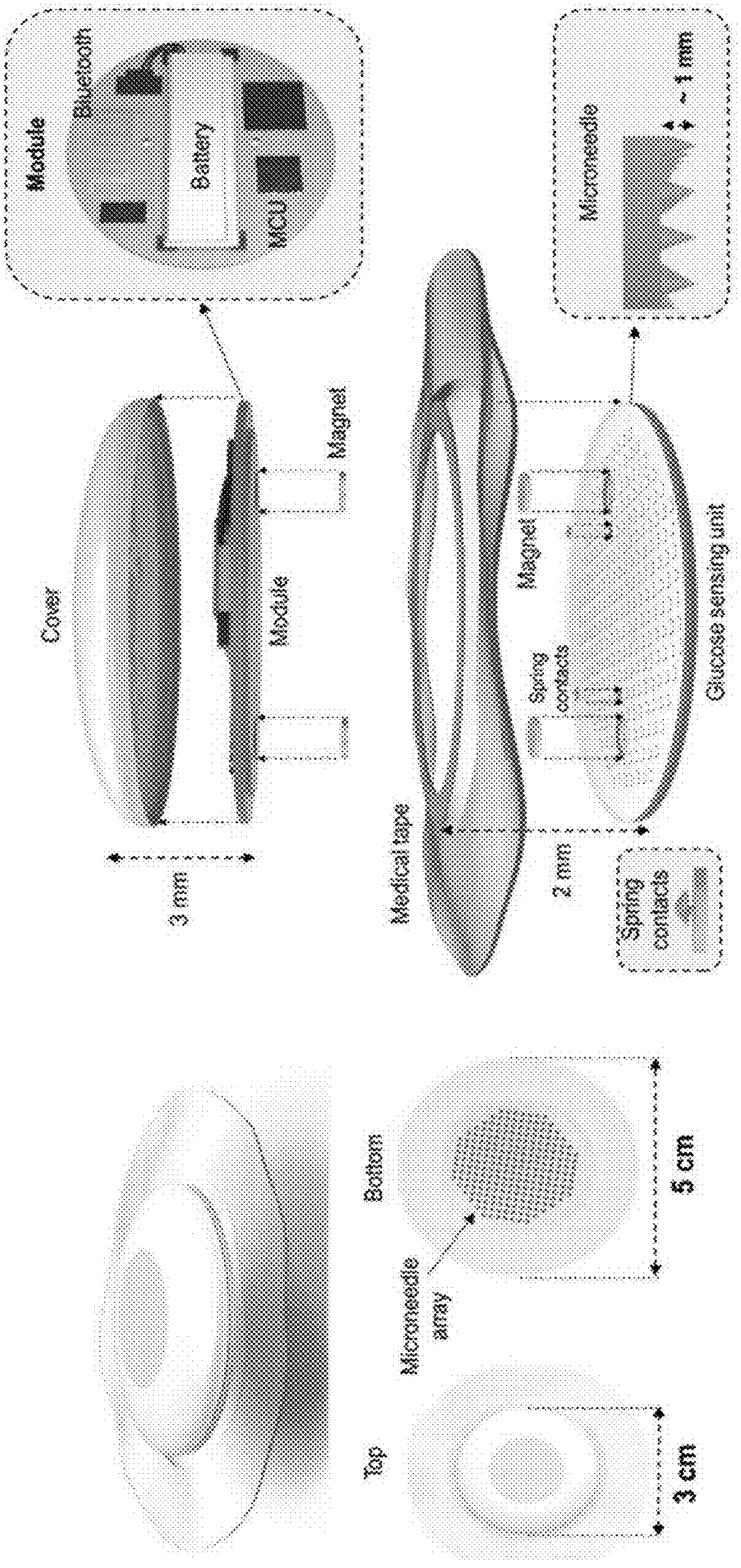
FIG. 1 is a diagram illustrating a glucose sensor according to an embodiment.

A voltage measurement type glucose sensor including a supercapacitor of the disclosure and a continuous glucose measurement method using the same will be described in detail. The terms used herein have been selected as general terms which are widely used at present in consideration of the functions of the disclosure, and this may be changed according to the intent of an operator skilled in the art, custom, or introduction of new technology. Unless technical and scientific terms used herein are defined otherwise, they have meanings generally understood by those skilled in the art to which the disclosure pertains.

In the specification and the appended claims, the terms such as "comprise" or "have" mean that there is a characteristic or a constituent element described in the specification, and unless otherwise particularly defined, a possibility of adding one or more other characteristics or constituent elements is not excluded in advance.

The singular form used in the specification and claims appended thereto may be intended to also include a plural form, unless otherwise indicated in the context. Also, the plural forms are intended to include the singular forms as well, unless the context clearly indicates the plural forms.

Further, a numerical range used in the present specification is meant to include its upper and lower limits and all possible combinations of all values falling within these limits, increments logically derived from the shapes and widths of defined ranges, all defined values thereof, and upper and lower limits of the numerical ranges defined in different types. Unless otherwise particularly defined in the present specification, all values falling out of this numerical range that may occur due to the rounding off of the experimental errors or values also fall within the defined numerical ranges.

In the specification and the appended claims, the terms "about", and the like are meant to encompass tolerances when such are present.

The term 'tissue fluid' in the specification refers to a liquid component that is located between animal tissues and serves as an environment for cells. Unless otherwise specified herein, it can be broadly interpreted as a higher-level concept encompassing tissue fluid which is liquid that fills between tissue cells, plasma, or blood.

Diabetes, which was previously considered a geriatric disease, is rapidly increasing in incidence among young people under the age of 40 due to environmental factors such as westernized eating habits, lack of exercise, and stress. If hyperglycemia persists, it is accompanied by various complications such as various cardiovascular diseases and strokes, so it is very important to prevent complications caused by hyperglycemia by continuously and closely monitoring a glucose status.

However, conventionally commercialized glucose sensors involve blood collection, which causes pain to a subject to be tested and makes systematic glucose management difficult because continuous glucose changes cannot be identified. To solve this problem, a continuous glucose monitoring (CGM) device has been developed that measures a glucose concentration in tissue fluid by inserting a microneedle into the skin.

The conventional continuous glucose monitoring (CGM) device is mainly composed of a three-electrode system and measures the current flowing between a working electrode and a counter electrode when a certain voltage is applied, thereby calculating a glucose concentration. This current measurement method has a problem in that device lifespan is seriously reduced because separate external power must be applied to the sensor.

To solve this problem, as disclosed in KR Registered Patent No. 10-2427230, a glucose sensor using a self-charging capacitor has been developed. However, such a glucose sensor qualitatively determines glucose information according to the intensity of light from a light emitting unit, so there is a problem in that accuracy when measuring glucose is low and the measured glucose information cannot be recorded, making it impossible to monitor trends in glucose changes.

Meanwhile, when transmitting and receiving glucose information to an external device through a wireless communication device, there is a problem that more power is consumed. For example, an NFC-type continuous glucose measuring device receives power once every five minutes to detect glucose concentration in tissue fluid, but tens of microwatts of power are consumed for one sensing, which places a large burden on the power source of the glucose sensor. Therefore, as the time interval for supplying power to measure glucose increases, there is a limit to closely monitoring changes in glucose.

Accordingly, after in-depth research, the present applicant has developed a voltage measurement type glucose sensor, which is self-driving without a need for a separate external power supply, improving the power efficiency and lifespan of the device, and can measure glucose with high accuracy by calculating glucose values using a voltage measurement method, and can closely monitor glucose changes in real time by transmitting and receiving measured glucose values in real time.

Hereinafter, the disclosure will be described with reference to the attached drawings.

As shown in FIG. 1, a glucose sensor according to the disclosure includes a microneedle array including a flat part and a plurality of microneedles located on one surface of the flat part; an enzyme layer located on a surface of the plurality of microneedles and including glucose oxidase; a supercapacitor located on the other side of the flat part; and a wireless communication module electrically connected to the supercapacitor.

The charge generated as glucose in the tissue fluid is oxidized through contact between the tissue fluid and the enzyme layer through the plurality of microneedles is stored in the supercapacitor, and the voltage of the supercapacitor is measured to quantify the glucose concentration. Accordingly, a self-driving glucose sensor can be implemented without the need for separate external power.

In addition, an amount of charge stored in the supercapacitor changes depending on the concentration of glucose included in the tissue fluid, and glucose levels may be measured with high accuracy by continuously measuring the voltage of the supercapacitor, which changes in proportion to the charge.

In one embodiment, the thickness of the glucose sensor may be 10 mm or less or 5 mm or less, preferably 3 mm or less, and may be, but not limited to, 0.1 mm or more. As the glucose sensor is self-driving, a separate battery and three-electrode system are not required for glucose measurement, enabling miniaturization of the sensor and providing excellent flexibility. Therefore, the glucose sensor can be manufactured in various shapes and sizes without restrictions on its form, and is advantageous because the discomfort and foreign body sensation felt by a user who wears the glucose sensor can be significantly reduced.

In one embodiment, the glucose sensor of the disclosure may not perform a glucose correction process through blood collection. The conventional continuous glucose monitoring device has the disadvantage of causing the user to feel pain after going through a glucose correction process through the blood collection. To solve this problem, a continuous glucose measuring device without glucose correction through blood collection has been developed, but there is a problem that it takes a long time to stabilize the device before sensing begins. On the other hand, the glucose sensor of the disclosure is not only a painless glucose sensor that does not require glucose correction through blood sampling, but also has the advantage of being convenient to use because the time required to stabilize the device is short, less than 30 minutes. More specifically, as will be described later, the voltage value of the supercapacitor and the glucose value may have a proportional relationship with very high linearity. Therefore, despite omitting the blood sugar correction process, it is advantageous to be able to sense the exact glucose concentration using the initial voltage value of the supercapacitor and the voltage change value due to the glucose concentration.

Figure 2:
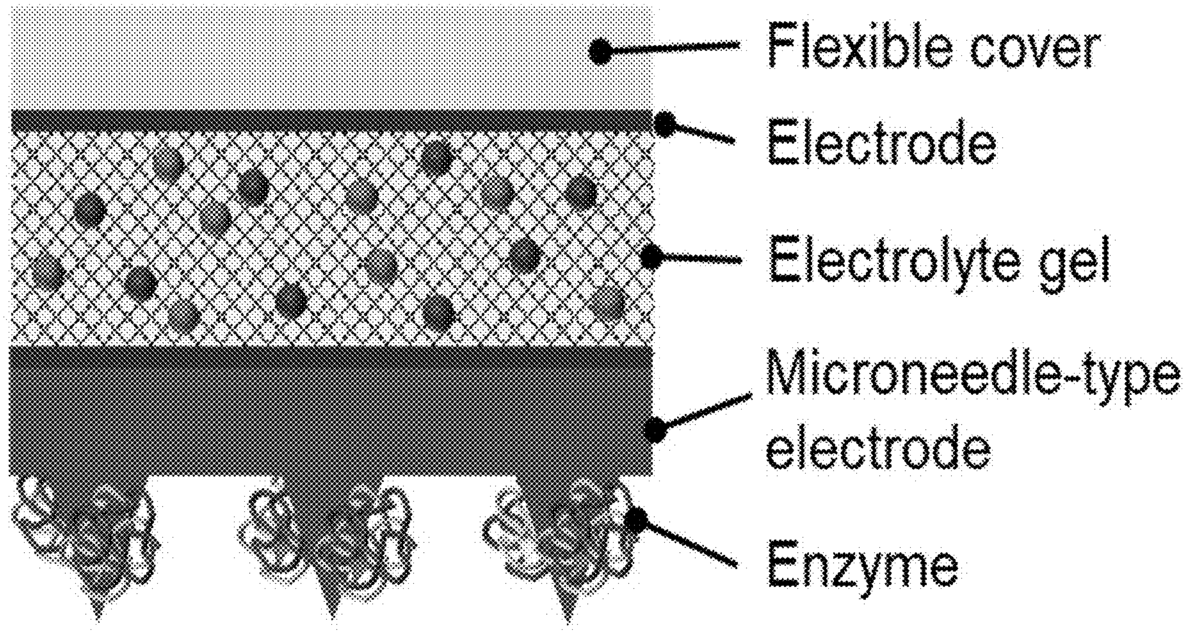
FIGS. 2 and 3 are schematic diagrams showing a microneedle array and a supercapacitor according to one embodiment.
Figure 3:
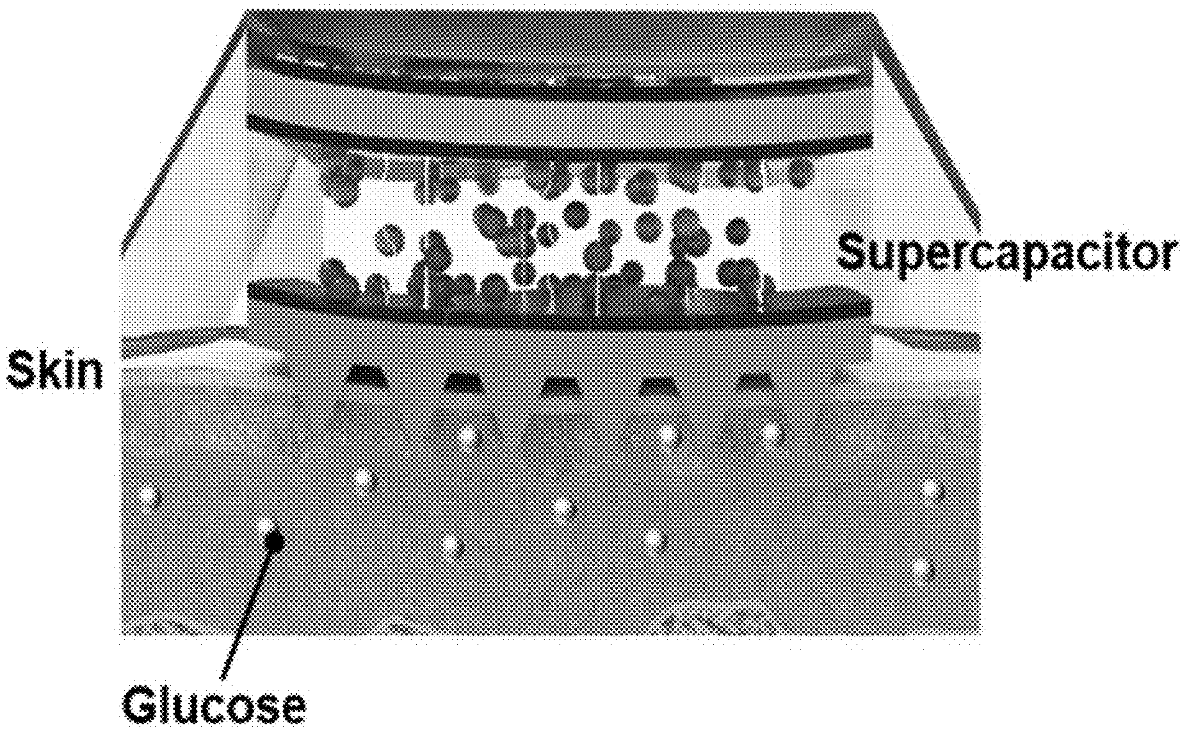

FIGS. 2 and 3 are schematic diagrams showing a supercapacitor, a microneedle array, and an enzyme layer according to one embodiment.

Referring to FIGS. 2 and 3, the microneedle array includes the flat part and the plurality of microneedles located on one side of the flat part, the supercapacitor is located on the other side of the flat part, and the enzyme layer including glucose oxidase may be located on the surface of the microneedle. When the microneedle is inserted into the skin, the tissue fluid and the enzyme layer come into contact, and the glucose included in the tissue fluid reacts with the glucose oxidase in the enzyme layer, generating an electric charge. The generated charge is stored in the supercapacitor through the microneedle array, and by measuring the voltage of the charged supercapacitor, glucose may be measured as a spontaneous response without the need to receive external power.

In a more specific example, the plurality of microneedles must pass through the stratum corneum of a target for glucose measurement and be inserted into the skin, so that the length of the microneedle is 50 to 1500 μm, specifically 100 to 1000 μm, to prevent bleeding and pain in the skin. The diameter of the bottom of the microneedle having the largest diameter may be 10 to 100 μm, specifically 30 to 80 μm, and the needle spacing of the microneedle array may be 50 to 1000 μm, specifically 200 to 800 μm, but is not limited thereto.

The shape of the microneedle may be any shape that can penetrate the skin, such as cone, pyramid, sphere, short-headed, wedge, or blade. In order to easily penetrate the skin, the microneedle preferably has a shape whose diameter becomes smaller as the microneedle moves away from the flat part.

The microneedle array including the flat part and microneedles preferably includes a conductive material so that the microneedle array can be electrically connected to the supercapacitor. More specifically, the microneedle array may have a structure having a coating layer coated with a conductive material on the surface of a flexible and highly biocompatible polymer such as polydimethylsiloxane (PDMS).

The conductive material preferably includes a conductive polymer to provide flexibility to the microneedle array. As an example, the conductive polymer may include one or more selected from the group consisting of polypyrrole, polyaniline, polythiophene, polyacetylene, and poly(3,4-ethylenedioxythiophene):poly(styrenesulfonate) (PEDOT:PSS).

In one embodiment, the microneedle array may further include a polymer containing a hydroxyl group (—OH) to ensure mechanical stability and flexibility, thereby forming a conductive polymer composite. A representative example of the polymer containing a hydroxyl group is polyvinyl alcohol (PVA). The composite can improve both the electrical conductivity and mechanical properties of the microneedle array through hydrogen bonding between the polymer containing hydroxyl groups and the conductive polymer.

Figure 4:
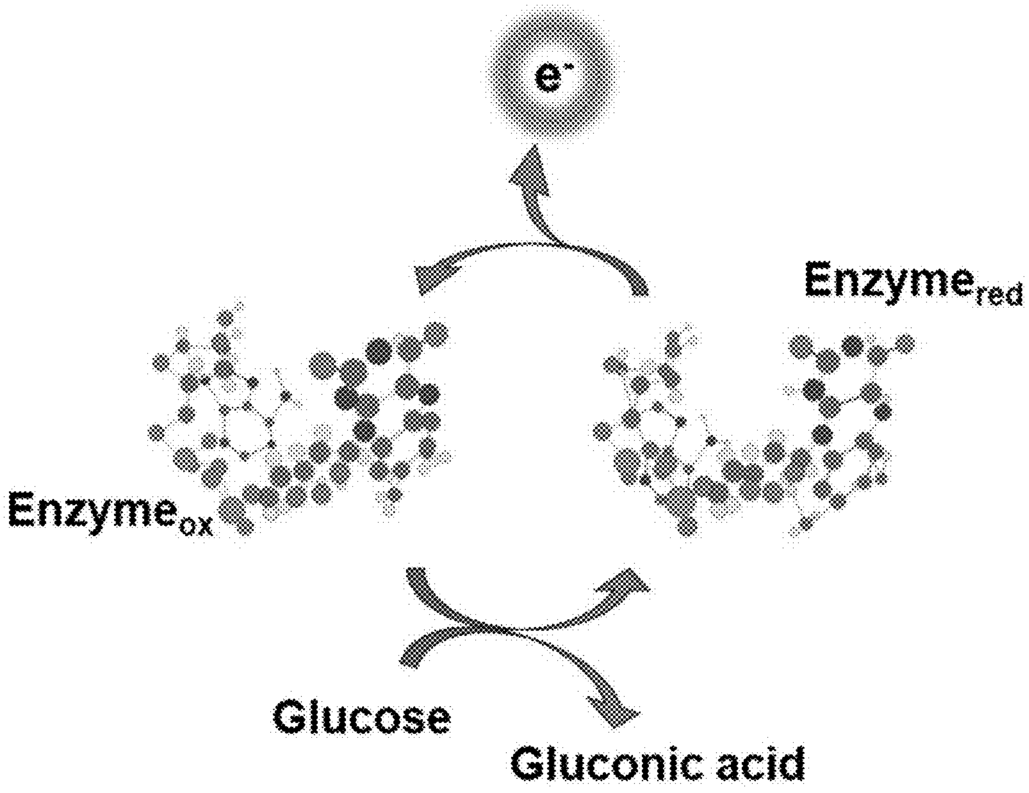
FIG. 4 is a diagram showing a glucose oxidation reaction process according to one embodiment.

By including the enzyme layer including glucose oxidase on the surface of the microneedle, a charge can be generated by oxidizing the glucose component contained in tissue fluid. Referring to FIG. 4, which shows the glucose oxidation process, glucose in tissue fluid is oxidized into gluconic acid by the glucose oxidase, and electrons can be generated from this. The electrons may be stored in the supercapacitor through the microneedle array to sense glucose.

In one embodiment, the enzyme layer is located on the surface of the microneedle, so that the glucose concentration in the tissue fluid can be measured in real time without the need to move the tissue fluid inside the glucose sensor. When the enzyme layer is located inside the microneedle array, tissue fluid must be moved from the microneedle to the inside of the sensor, which causes a time difference in calculating glucose levels, the structure of the sensor becomes complicated, and there is a concern that the durability of the sensor may be reduced by tissue fluid.

On the other hand, the glucose sensor of the disclosure, which includes the enzyme layer on the surface of the microneedle, does not require tissue fluid to penetrate into the sensor, improving the durability of the glucose sensor. Therefore, advantageously, the user's glucose in blood can be detected in real time, allowing immediate monitoring of changes in glucose.

In one embodiment, the amount of charge generated by glucose oxidation may be controlled by adjusting the thickness of the enzyme layer and the concentration of the enzyme. As a non-limiting example, the thickness of the enzyme layer may be 100 to 1000 nm, specifically 500 to 700 nm, and the concentration of glucose oxidase may be 100 U/ml to 10 kU/ml, specifically 500 U/ml to 1 kU/ml.

When the enzyme layer is inserted into the human body while exposed to the outside, there is a risk of the enzyme layer being exposed to tissue fluid and collapsing. Accordingly, a problem occurs in which enzymes escape into the body, and glucose levels may be measured inaccurately when measured over a long period of time.

Accordingly, the enzyme layer may further include a crosslinker to increase the anchoring force of the glucose oxidase located on the surface of the microneedle. Even when the glucose oxidase located on the surface of the microneedle comes into contact with tissue fluid through the crosslinker, the glucose oxidase does not escape from the microneedle and is maintained for a long period of time, thereby improving the lifespan of the sensor. The crosslinker may be any substance that can connect single enzymes by binding to the amino group contained in the enzyme. As a non-limiting example, the crosslinker is an aldehyde-based compound containing two or more functional groups, and as the crosslinker, there may be glutaraldehyde. According to another aspect, the aldehyde-based compound may be bound to the surface of the microneedle. The aldehyde group located on the surface of the microneedle is bound to the glucose oxidase and may not be separated from the surface of the microneedle.

In addition, a porous membrane located on the enzyme layer may be further included to prevent the enzyme layer from collapsing due to exposure to the external environment. The porous membrane prevents the enzyme layer from coming into direct contact with tissue fluid, effectively preventing the enzyme layer from collapsing and preventing the enzyme from being deteriorated by the external environment. Therefore, since the glucose can be oxidized without the enzyme layer collapsing within the tissue fluid, the glucose in blood can be measured with high precision over a long period of time.

The porous membrane is uniformly coated on the upper portion of the enzyme layer, so that the shape of the microneedle can be kept constant. Specifically, if the shape of the microneedle is conical, the conical shape can be maintained even when the enzyme layer and porous membrane are located on the surface of the microneedle.

In this case, a non-limiting example of the thickness ratio of the enzyme layer:porous membrane may be 1:1 to 10, specifically 1:2 to 5. In this range, the glucose can pass through the porous membrane and move to the enzyme layer, and at the same time, the porous membrane can prevent the collapse of the enzyme layer.

The average pore size of the porous membrane may be 100 to 1000 nm, specifically 200 to 500 nm. The porous membrane with an average pore size in the above range may selectively supply only the glucose component of tissue fluid to the enzyme layer, excluding other components, enabling more precise glucose sensing.

In one embodiment, the average porosity of the porous membrane may be 30 to 80%, specifically 50 to 60%. The porous membrane having an average porosity in the above range may measure the glucose with high accuracy by allowing an appropriate amount of glucose to flow into the tissue fluid.

As the porous membrane, any biocompatible material may be used without limitation, but the porous membrane may preferably be a hydrophobic fluorine-based polymer. Specifically, the hydrophobic fluorine-based polymer may include a PVDF-based polymer, and more specifically, the porous membrane may include polyvinylidene fluoride (PVDF). The PVDF is advantageous because it is easy to control the amount of glucose delivered to the enzyme layer, and despite its porous structure, it can exhibit mechanical properties that can stably protect the enzyme layer. In addition, the porous membrane including a hydrophobic fluoropolymer is chemically stable even when penetrated into the skin, and is more advantageous because the pore size and porosity of the porous membrane can be easily controlled when the porous membrane is manufactured with the hydrophobic fluoropolymer. For example, the PVDF porous membrane may be manufactured by a solvent-non-solvent induced phase separation method, and since the method is known in the art, detailed description will be omitted.

In one embodiment, the porous membrane may include a first coating film including a PVDF-based polymer and positioned on an enzyme layer, and a second coating film positioned on the first coating film and including an ion-conductive fluorine-based polymer. The porous membrane including the first coating film and second coating film may control the amount of glucose moving to the enzyme layer by the second coating film, and the glucose that reaches the first coating film through the second coating film is uniformly distributed across the entire first coating film, enabling more precise and reliable glucose measurement over a long period of time. In detail, the ion conductive fluorine-based polymer may be Nafion, and the thickness ratio of the first coating film to second coating film may be 1:1 to 0.1 or 1:0.8 to 0.3, but the disclosure is not limited thereto.

The supercapacitor has one electrode electrically connected to the microneedle array and may store charges transferred through the microneedle array.

In one embodiment, the structure of a supercapacitor, as shown in FIG. 2, may include a first substrate, a second substrate spaced apart from the first substrate, a first current collector located on the first substrate, a second current collector disposed spaced apart from the first current collector, a first electrode located on one surface of the first current collector, a second electrode located on one surface of the second current collector and spaced apart from the first electrode, and an electrolyte located between the first electrode and the second electrode.

In detail, the flat part of the microneedle array may serve as the first substrate. The second substrate may include polydimethylsiloxane (PDMS) to maintain flexibility, but is not limited thereto. The thickness of the second substrate may be 1000 μm or less or 900 μm or less, preferably 800 μm or less, and as an non-limiting example, the thickness of the second substrate may be 100 μm or more. Within the above thickness range, the flexibility of the glucose sensor may be maintained while simultaneously supporting the current collector and electrode, which will be described later.

The first and second current collectors may include a conductive material, for example, a conductive oxide such as indium tin oxide (ITO) or a silver nanowire, but are not limited thereto. The thickness of the first current collector and second current collector may independently be 100 μm or less, 80 μm or less, or 60 μm or less, preferably 50 μm or less, and as non-limiting example, the thickness of the first current collector may be 5 μm or more. In the above thickness range, the current collector may not be separated from the substrate due to mechanical deformation.

The first and second electrodes may include carbon-based materials, conductive polymers, or combinations thereof. A composite including a carbon-based material and conductive polymer is used as the first and second electrode material, thereby providing excellent electrical conductivity, light-weight properties, and flexibility. Accordingly, surface cracks caused by mechanical deformation can be prevented.

As an example, the carbon-based material may include one or more selected from the group consisting of activated carbon, carbon nanotube, graphene, and reduced graphene oxide (rGO). The conductive polymer may include one or more selected from the group consisting of polypyrrole, polyaniline, polythiophene, polyacetylene, and poly(3,4-ethylenedioxythiophene):poly(styrenesulfonate) (PEDOT:PSS). However, the disclosure is not limited by the specific types of the first electrode and second electrode.

The thickness of the first electrode and second electrode may independently be 100 μm or less, 80 μm or less, or 60 μm or less, preferably 50 μm or less, and as an non-limiting example, the thickness may be 5 μm or more. In the above thickness range, the electrode may not be separated from the current collector due to mechanical deformation.

In one embodiment, the electrolyte may be a gel polymer electrolyte that has thinner thickness and improved flexibility without the need for a separate separator, has no risk of explosion due to electrolyte leakage or short circuit of the electrode, and has excellent mechanical stability. The gel-type polymer electrolytes may include polymers and electrolytes. The polymer may be any polymer containing a hydroxyl group (—OH) and may preferably include polyvinyl alcohol (PVA). The electrolyte may include acids, bases, or inorganic salts such as sulfuric acid ($H_2SO_4$), phosphoric acid ($H_3PO_4$), potassium hydroxide (KOH), sodium hydroxide (NaOH), and potassium chloride (KCl).

The thickness of the electrolyte may be 0.05 to 2 mm or 0.08 to 1.5 mm, and preferably 0.1 to 1 mm. Within the above thickness range, flexibility can be secured and short circuiting between the first and second electrodes may not occur.

The glucose concentration may be quantified by measuring the voltage value of the supercapacitor according to the amount of charge charged in the supercapacitor. In this case, the circuit that flows the charge of the charged supercapacitor to the outside further includes a switch, allowing glucose levels to be sensed at a faster rate. As a more specific example, the circuit may include a timer and a switch, and the switch may repeat ON/OFF at regular time intervals. When the switch is switched from an OFF state to an ON state at certain intervals, the circuit connecting both electrodes of the supercapacitor is connected, and the first and second electrodes are short-circuited to discharge the supercapacitor, so that the glucose concentration may be calculated by measuring the voltage value of the capacitor. If the switch is switched from the ON state to the OFF state after a certain period of time, the circuit connecting both electrodes of the supercapacitor may be broken and the supercapacitor may be charged. As the above process is repeated, glucose may be sensed accurately at high speed.

In one embodiment, the calculated glucose value may be transmitted to an external device through a wireless communication module electrically connected to the supercapacitor.

Figure 5:
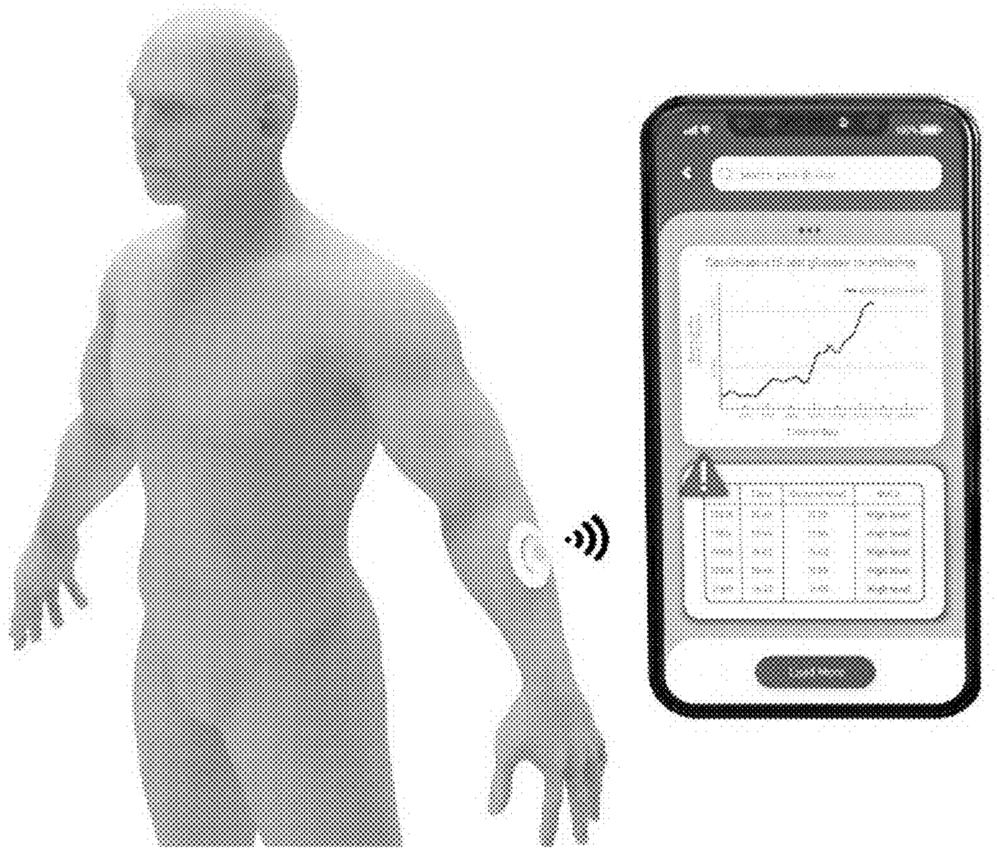
FIG. 5 is a schematic diagram showing a wireless communication process of a glucose sensor according to one embodiment.

FIG. 5 is a schematic diagram showing a wireless communication process of a glucose sensor according to an embodiment. As shown in FIG. 5, the glucose level is transmitted to an external device through the wireless communication module, and the device that receives the glucose level automatically records the glucose level so that the user can easily monitor the glucose level.

In one embodiment, the wireless communication module may be a short-range communication module. Specifically, the wireless communication module may include infrared communication, WiFi, NFC, Bluetooth, etc., and preferably includes Bluetooth.

The disclosure includes a continuous glucose measurement method using the above-described glucose sensor.

The continuous glucose measurement method according to the disclosure includes the steps of (S1) inserting the above-described glucose sensor into the skin to collect tissue fluid; (S2) storing the charge generated by oxidation of glucose contained in the tissue fluid in the supercapacitor; (S3) quantifying a glucose level by measuring the voltage change of the supercapacitor; and (S4) transmitting the glucose level to an external device.

As described above, in the continuous glucose measurement method using the glucose sensor of the disclosure, the glucose sensor is self-driven without the need to apply external power, so no power is consumed to measure the glucose concentration, so glucose can be measured with low power. Therefore, the power efficiency of the device can be increased and battery power can be saved. Therefore, it is advantageous to improve device lifespan because limited battery capacity can be used for a longer period of time.

In addition, a typical continuous glucose measuring device that measures glucose concentration by receiving external power consumes a lot of power for glucose sensing, so it has the disadvantage of not being able to closely observe changes in glucose as the time interval for measuring glucose increases.

On the other hand, the continuous glucose measurement method using the glucose sensor of the disclosure measures the user's glucose in real time because no power is consumed for glucose sensing, and transmits the glucose level to an external device in real time through a wireless communication module to track changes in glucose. Accordingly, the disclosure is advantageous in that it is possible to accurately and quickly determine changes in glucose levels.

Specifically, the electrons generated by oxidation of glucose contained in tissue fluid in the enzyme layer move to the first electrode of the supercapacitor, thereby increasing the electron density of the first electrode. This causes a potential difference between the first and second electrodes of the supercapacitor, and the voltage of the supercapacitor may increase depending on the charging principle of the supercapacitor. Since the amount of charge generated by a chemical reaction varies depending on the glucose concentration, the voltage value of the supercapacitor also varies, allowing the glucose concentration to be distinguished. In addition, it is advantageous because glucose levels may be calculated using the voltage value of the supercapacitor, providing users with quantified glucose information with high accuracy.

Figure 6:
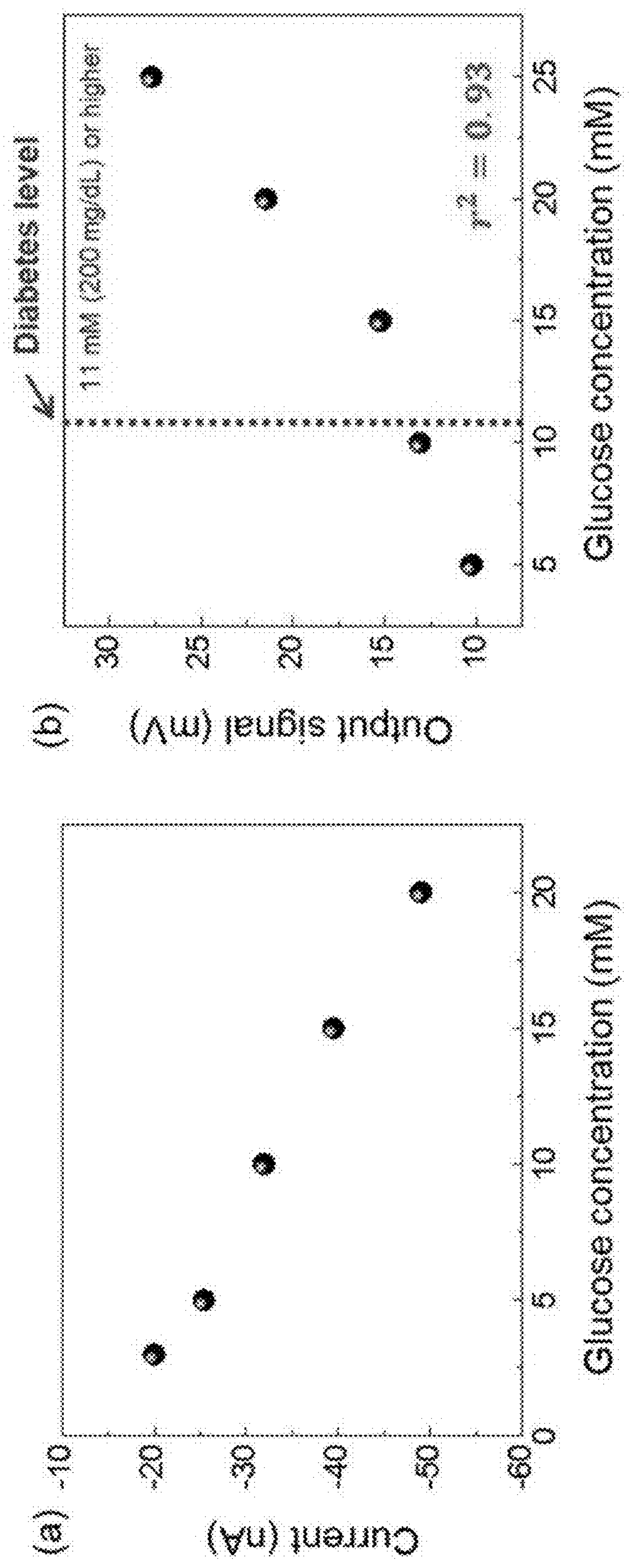
FIG. 6 is a graph measuring (a) current change and (b) voltage change of a supercapacitor according to glucose concentration of a glucose sensor according to one embodiment.

FIG. 6 is a graph showing measurements of (a) current change and (b) voltage change of a supercapacitor according to glucose concentration when glucose is measured using a glucose sensor according to an embodiment.

Referring to (a) in FIG. 6, as the glucose concentration increases, the amount of charge also increases, confirming that the glucose contained in the tissue fluid is oxidized by the enzyme layer and electrons may be spontaneously generated without applying external power. In FIG. 6, (b) is a graph showing the measurement of the output voltage value according to glucose concentration. It shows high linearity between glucose concentration and output signal, confirming that the glucose sensor of the disclosure may accurately measure the user's glucose with high precision.

Hereinabove, although the disclosure is described by specific matters, exemplary embodiments, and drawings, they are provided only for assisting in the entire understanding of the disclosure. Therefore, the disclosure is not limited to the exemplary embodiments. Various modifications and changes may be made by those skilled in the art to which the disclosure pertains from this description.

Therefore, the spirit of the disclosure should not be limited to the above-described examples, and the following claims as well as all modified equally or equivalently to the claims are intended to fall within the scopes and spirits of the disclosure.

What is claimed is:

1. A glucose sensor, comprising:

a microneedle array including a flat part and a plurality of microneedles located on one side of the flat part;

an enzyme layer located on a surface of the plurality of microneedles and including glucose oxidase;

a supercapacitor located on another side of the flat part;

a wireless communication module electrically connected to the supercapacitor; and a circuit connected to the supercapacitor and including a timer and a switch, the circuit being configured to discharge the supercapacitor by short-circuiting a first electrode and a second electrode of the supercapacitor through the switch at predetermined time intervals.

2. The glucose sensor of claim 1, wherein the microneedle array is electrically connected to one electrode of the supercapacitor.

3. The glucose sensor of claim 1, wherein a charge generated by oxidation of glucose in the enzyme layer is stored in the supercapacitor.

4. The glucose sensor of claim 1, wherein the glucose sensor operates without separate external power.

5. The glucose sensor of claim 1, wherein the microneedle array includes a conductive polymer.

6. The glucose sensor of claim 1, further comprising a porous membrane located on the enzyme layer.

7. The glucose sensor of claim 6, wherein the porous membrane includes a PVDF-based polymer.

8. The glucose sensor of claim 6, wherein an average pore size of the porous membrane is in a range of 200 to 500 nm.

9. The glucose sensor of claim 6, wherein an average porosity of the porous membrane is in a range of 50 to 60%.

10. The glucose sensor of claim 1, wherein the supercapacitor includes:

the first electrode located on one surface of a first current collector;

the second electrode located on one surface of a second current collector and spaced apart from the first electrode; and an electrolyte located between the first electrode and the second electrode.

11. The glucose sensor of claim 10, wherein the electrolyte includes a gel polymer electrolyte.

12. The glucose sensor of claim 1, wherein the wireless communication module includes Bluetooth.

13. A continuous glucose measurement method, comprising:

inserting a glucose sensor into a skin to collect tissue fluid, wherein the glucose sensor comprises a microneedle array including a flat part and a plurality of microneedles located on one side of the flat part, an enzyme layer located on a surface of the plurality of microneedles and including glucose oxidase, a supercapacitor located on another side of the flat part, a wireless communication module electrically connected to the supercapacitor, and a circuit connected to the supercapacitor and including a timer and a switch, the circuit being configured to discharge the supercapacitor by short-circuiting a first electrode and a second electrode of the supercapacitor through the switch at predetermined time intervals;

storing charge generated by oxidation of glucose contained in the tissue fluid in the supercapacitor;

quantifying a glucose level by periodically discharging the supercapacitor through the circuit, and measuring a voltage change of the supercapacitor; and transmitting the glucose level to an external device.

14. The continuous glucose measurement method of claim 13, wherein the external device records the glucose level in real time.

* * * * *